(12) United States Patent
Devlin, Sr.

(10) Patent No.: US 8,038,941 B2
(45) Date of Patent: Oct. 18, 2011

(54) METHOD FOR INCREASING THROUGHPUT IN AN AUTOMATIC CLINICAL ANALYZER BY DUPLICATING REAGENT RESOURCES

(75) Inventor: William Jackson Devlin, Sr., Lincoln University, PA (US)

(73) Assignee: Siemens Healthcare Diagnostics Inc., Deerfield, IL (US)

( * ) Notice: Subject to any disclaimer, the term of this patent is extended or adjusted under 35 U.S.C. 154(b) by 0 days.

(21) Appl. No.: 12/913,149

(22) Filed: Oct. 27, 2010

(65) Prior Publication Data

US 2011/0044854 A1 Feb. 24, 2011

Related U.S. Application Data

(62) Division of application No. 10/817,545, filed on Apr. 2, 2004, now Pat. No. 7,842,504.

(51) Int. Cl.
*G01N 21/00* (2006.01)
(52) U.S. Cl. .............................. 422/64; 422/63; 422/509
(58) Field of Classification Search .............. 422/63–65, 422/501, 509
See application file for complete search history.

(56) References Cited

U.S. PATENT DOCUMENTS

| | | | |
|---|---|---|---|
| 5,087,423 | A | 2/1992 | Ishibashi |
| 5,434,083 | A | 7/1995 | Mitsumaki et al. |
| 5,482,861 | A | 1/1996 | Clark et al. |
| 5,679,309 | A | 10/1997 | Bell et al. |
| 5,730,939 | A | 3/1998 | Kurumada et al. |
| 5,846,491 | A | 12/1998 | Choperena et al. |
| 5,985,672 | A | 11/1999 | Kegelman et al. |
| 6,019,945 | A | 2/2000 | Ohishi et al. |
| 6,022,746 | A | 2/2000 | Fritchie et al. |
| 6,284,475 | B1 | 9/2001 | Rand |
| 6,599,749 | B1 | 7/2003 | Kodama et al. |
| 6,649,128 | B1 | 11/2003 | Meyer et al. |
| 6,701,096 | B2 | 3/2004 | Arai et al. |
| 6,723,288 | B2 | 4/2004 | Devlin et al. |
| 6,730,517 | B1 | 5/2004 | Koster et al. |
| 7,101,715 | B2 | 9/2006 | Devlin et al. |
| 7,270,784 | B2 | 9/2007 | Vuong et al. |
| 2003/0040117 | A1* | 2/2003 | Devlin, Sr. ............ 436/46 |

* cited by examiner

*Primary Examiner* — Jill Warden
*Assistant Examiner* — Dwayne K Handy
(74) *Attorney, Agent, or Firm* — Leland K. Jordan

(57) ABSTRACT

A method for maximizing analyzer throughput irregardless of the mix in demand of different assays to be conducted by duplicating the reagents required to conduct selected assays in at least two separate reagent servers and also enabling newly incoming selected assays to be conducted using reagents from whichever reagent server has the smaller backlog of such high-volume assays.

4 Claims, 10 Drawing Sheets

| Operation | Minutes | Seconds | Type A Assay | Type B Assay | Type C Assay |
|---|---|---|---|---|---|
| R1 | -.036 | -21.6 | R1 | R1 | R1 |
| RX | -.006 | -3.6 |  |  |  |
| S | 0.00 | 0.0 | S | S | S |
| RX | 0.66 | 39.6 | Rd |  |  |
| RX | 1.38 | 82.8 | Rd |  |  |
| R2 | 2.10 | 126.0 | Rd |  |  |
| Rd | 3.00 | 180.0 | Rf | Rd |  |
| Rd | 3.66 | 219.6 |  | Rd |  |
| Rd | 6.00 | 360.0 |  | Rd | Rf |
| Rd | 7.26 | 435.6 |  | Rd | Rd |
| Rd | 9.66 | 579.6 |  | Rd | Rd |
| Rd | 10.86 | 651.6 |  | Rd | Rf |

R1 = 1st Reagent Addition
R2 = 2nd Reagent Addition
Rx = possible 3rd Reagent Addition
S  = Sample Addition
Rd = Read by Devices 86
Rf = Final Read

Fig. 7

METHOD FOR INCREASING THROUGHPUT IN AN AUTOMATIC CLINICAL ANALYZER BY DUPLICATING REAGENT RESOURCES

CROSS-REFERENCE TO RELATED APPLICATION

This application is a Divisional of U.S. patent application Ser. No. 10/817,545, filed on Apr. 2, 2004.

FIELD OF THE INVENTION

The present invention relates to a method and apparatus for automatically processing a patient's biological fluids such as urine, blood serum, plasma, cerebrospinal fluid and the like. In particular, the present invention provides an improved method to increase the throughput of patient samples in a clinical analyzer adapted to perform a number of different clinical assays.

BACKGROUND OF THE INVENTION

Various types of tests related to patient diagnosis and therapy can be performed by analysis assays of a sample of a patient's infections, bodily fluids or abscesses. Such patient samples are typically placed in sample vials, extracted from the vials, combined with various reagents in special reaction cuvettes or tubes, frequently incubated, and analyzed to aid in treatment of the patient. In typical clinical chemical analyses, one or two assay reagents are added at separate times to a liquid sample, the sample-reagent combination is mixed and incubated within a reaction cuvettes. Analytical measurements using a beam of interrogating radiation interacting with the sample-reagent combination, for example turbidimetric or fluorometric or absorption readings or the like, are made to ascertain end-point or rate values from which an amount of analyte may be determined using well-known calibration techniques.

Although automated analyzers for chemical, immunochemical and biological testing of samples are available, analytical clinical technology is challenged by increasing needs for improved levels of analysis. In addition, due to increasing pressures on clinical laboratories to reduce cost-per-reportable result, there continues to be a need for improvements in the overall cost effectiveness of clinical analyzers. In particular, sample analysis may be more effective by increasing assay throughput thereby reducing the cost thereof.

An important contributor to maintaining high assay throughput of automatic analyzers is the ability to quickly process a plurality of samples through a variety of different assay process and signal measurement steps. If no premium was placed on space within health care facilities, clinical analyzers could be designed for high-speed throughput by simply spacing apart multiple numbers of rugged components in dedicated positions to carry out different assay technologies. This is not feasible and even further, there are different standards for evaluating the rate of throughput of a clinical analyzer. A volume throughput measurement relates to how much time is required for all assays on all samples to be tested to be completed. Alternately, an assay throughput measurement may relate to how much time is required for a specified assay of a specified sample to be completed. For example, in terms of volume throughput, 1000 patient samples may be completed during 4 hours but the first result may be available only 3 hours after start-up. However, in terms of assay throughput, a first assay result may be available 30 minutes after a sample is placed on an analyzer but the last result may be available only 10 hours after start-up. Such diverse values in analyzer throughput are not generally acceptable to laboratory personnel and therefore automatic analyzers are required to simultaneously have a high volume processing throughput in terms of sample assays/hour as well as a fast turn-around time to the first available reportable result.

One common method of scheduling assay resources to maximize throughput is based upon the use of a predetermined fixed cycle where all assay resources in the instrument operate within a fixed length, predetermined cycle. Systems having this scheduling method have each assay resource returning to a predetermined location at the end of each cycle. Automated analyzers which use a predetermined fixed cycle method of scheduling the timing of resources also have single chronology operation. Each container of sample proceeds through each of the operational stations of the analyzer in the same order. The Stratus® II Immunoassay System is such an automated immunoassay system and is described in Volume 41 of the J. Clin. Immun. In the Stratus analyzer, a generally circular reaction carousel moves forward a fixed distance for each cycle of the system, indexing sequentially in a clockwise fashion past an incubation stage, a washing stage and a reading stage. A similar process is described in U.S. Pat. No. 5,575,976 in which each assay resource has a predetermined fixed operation window within the fixed processing cycle. Consequently, the control for one assay resource can rely on predetermined timing of other dependent and independent assay resources. Therefore, analyte tests having variable protocols and that are processed by moving reaction vessels in different chronologies can be interleaved if their assay resource requirements do not conflict, i.e., analyte tests with shorter processing time can be entered after those with longer processing times and the shorter analyte test can finish first. This can be achieved because the means of transporting reaction vessels containing assay constituents can present reaction vessels to the necessary assay resources in whatever order is required, regardless of entry order.

U.S. Pat. No. 5,434,083 uses a rotating reaction vessel train in which an analysis time of each of the test items is set to correspond to the number of times of circulation (number of cycles) of the reaction vessels on the reaction line. A reaction vessel renew device is selectively controlled for each reaction vessel in accordance with the number of cycles. Thus, a test item which requires a short reaction time is processed in a smaller number of cycles of the reaction line and a test item which requires a long reaction time is processed in a larger number of cycles The analyzer can sequentially process a plurality of test items which require different reaction times for one sample.

U.S. Pat. No. 5,482,861 operates an automated continuous and random access analytical system capable of simultaneously effecting multiple assays of a plurality of liquid samples wherein scheduling of various assays of the plurality of liquid samples is followed by creating a unit dose and separately transferring a first liquid sample and reagents to a reaction vessel without initiation of an assay reaction sequence, followed by physical transfer of the unit dose disposable to a processing workstation, whereby a mixture of the unit dose disposable reagents and sample are achieved during incubation.

U.S. Pat. No. 5,576,215 operates a biological analyzer wherein instrument systems used to perform assays of the biological samples loaded into the analyzer are operated in accordance with a schedule developed by a scheduler routine. The scheduler routine determines interval periods between operations performed by the analyzer instrument systems on each biological sample as a function of an entered load list unless a fixed interval period between the operations is required and schedules instrument system operations and the determined interval periods. The biological system analyzer performs assays of the biological samples by operating the analyzer instrument systems in accordance with the developed schedule.

U.S. Pat. No. 5,679,309 discloses a method for controlling an analyzer including a rotatable, circular reaction carousel which has circumferentially spaced cuvettes. Each cuvette, according to the menu of the analyzer, is designated to receive a selected reagent and a selected sample for reaction and analysis and, post-analysis, be washed for re-use. A drive indexes the reaction carousel to position the cuvettes according to the menu and in proper sequence, for receipt of reagent, sample and for wash and for analysis. When photometric analysis is used, the drive operates on a sequence of a spin cycle, during which the reaction carousel is spun for photometric analysis of reacting cuvettes, and a park cycle, for a period of time for insertion of reactant, sample and/or for wash.

U.S. Pat. No. 5,846,491 increases throughput by employing an analyzer control system with means for allocating assay resources to one of a number of reaction vessels as a function of the time cycle for that vessel and transferring reaction vessels directly from one assay resource station to another according to a chronology selected from a plurality of different predetermined chronologies.

U.S. Pat. No. 5,985,672 also addresses the need for high-speed processing by employing a pre-processor for use in performing immunoassays on samples for analytes in the sample employing concentrically positioned incubating and processing carousels. A single transfer station permits reaction vessels containing sample and reagents to be moved between the carousels. The samples are separated, washed and mixed on the processing carousel and incubated on the incubating carousel thus speeding up processing throughput.

Another scheduling method used in automated analyzers does not use a fixed cycle, instead using a scheduling method referred to as "kitting." U.S. Pat. No. 6,096,561 discloses an automated continuous and random access analytical system, capable of simultaneously effecting multiple assays of a plurality of liquid samples wherein various assays are scheduled for a plurality of liquid samples. Through kitting, the system is capable of creating a unit dose by separately transferring liquid sample and reagents to a reaction vessel without initiation of an assay reaction sequence. From the kitting means, multiple, kitted unit dose disposables are transferred to a process area, where an aliquot is mixed for each independent sample with one or more liquid reagents at different times in a reaction vessel to form independent reaction mixtures. Independent scheduling of kitting and mixing is achieved during incubation of the multiple reaction mixtures, simultaneously and independently. The system is capable of performing more than one scheduled assay in any order in which a plurality of scheduled assays is presented. The incubated reaction mixtures are analyzed independently and individually by at least two assay procedures which are previously scheduled.

From this discussion of the art state in automated clinical analyzers, it may be seen that while considerable progress has been made toward increasing analyzer throughput, there remains an unmet need for a system and apparatus that provides a high volume throughput for different types of assays, particularly in view of the fact that throughput for different peak load times within a health care facility can vary depending on what assays are requested to be performed and how those assays are performed on an analyzer. In particular, assay demand patterns for early morning patient samples are usually found to be different from assay demand patterns for mid-day samples and little attention has been given as to how this disparity in assay demand patterns may be advantageously addressed.

SUMMARY OF THE INVENTION

Clinical analyzers typically include an assay reaction carousel for holding reaction cuvettes which is rotated in stepwise movements in a constant circular direction, the stepwise movements separated by stationary dwell times, during which dwell time an assay operational device may perform different operation on an assay mixture contained within the reaction cuvette. An analyzer on which the present invention may be performed has at least two separate reagent servers or inventories of reagents as well as a plurality of conventional assay operation stations, such as sensors, reagent add stations, mixing stations, separation stations, and the like. The objective of maximizing analyzer throughput regardless of the mix of different assays to be conducted is difficult to achieve because health care facilities typically experience a first demand pattern at the beginning of a day and a different second demand pattern towards the middle of a day. Due to the practicality of performing routine assays on new patient samples most often beginning early in a day, a larger percentage of high volume "routine morning" assays are performed by the analyzer at the beginning of a day in contrast to a larger percentage of lower volume "esoteric afternoon" assays being requested later in the day. This difference in demand patterns may be explained in that after a series of "routine morning" assays have been analyzed by a physician, the results frequently indicate the need for additional diagnostic testing and therefore "esoteric afternoon" assays are ordered. The principal object of the present invention is to provide a method for using an automatic clinical analyzer in a manner that achieves a maximum high throughput irregardless of the different assay demand patterns required to be performed by the analyzer at different times of a day. This invention achieves its stated object by duplicating the reagents required to conduct at least one high-volume assay in at least two separate reagent servers so as to increase throughput regardless of whether the incoming assay demand pattern has a larger percentage of a first group of assays (e.g., high volume "routine morning" assays) or a larger percentage of a second group of different assays (e.g., lower volume "esoteric afternoon" assays). In addition, the present invention enables newly incoming high-volume assays to be conducted using reagents from whichever of at least two reagent servers has the smaller backlog of assays.

BRIEF DESCRIPTION OF THE DRAWINGS

The invention will be more fully understood from the following detailed description thereof taken in connection with the accompanying drawings which form a part of this application and in which:

FIG. 7 is a chart showing the time sequence for various operational events performed for different types of assays conducted by the analyzer of FIG. 1;

DETAILED DESCRIPTION OF THE INVENTION

Figure 1:
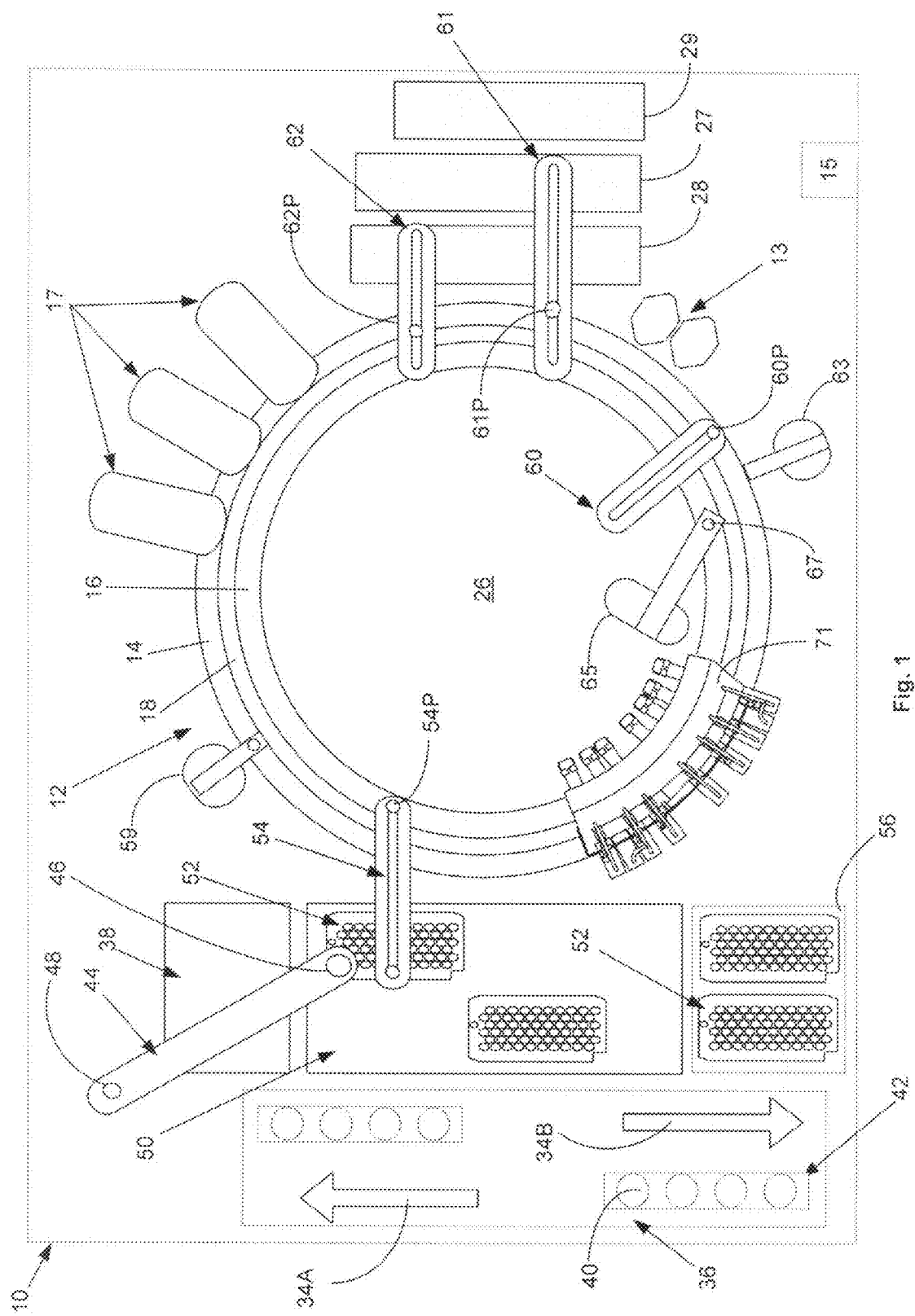
FIG. 1 is a schematic plan view of an automated analyzer in which the present invention may be practiced.
Figure 2:
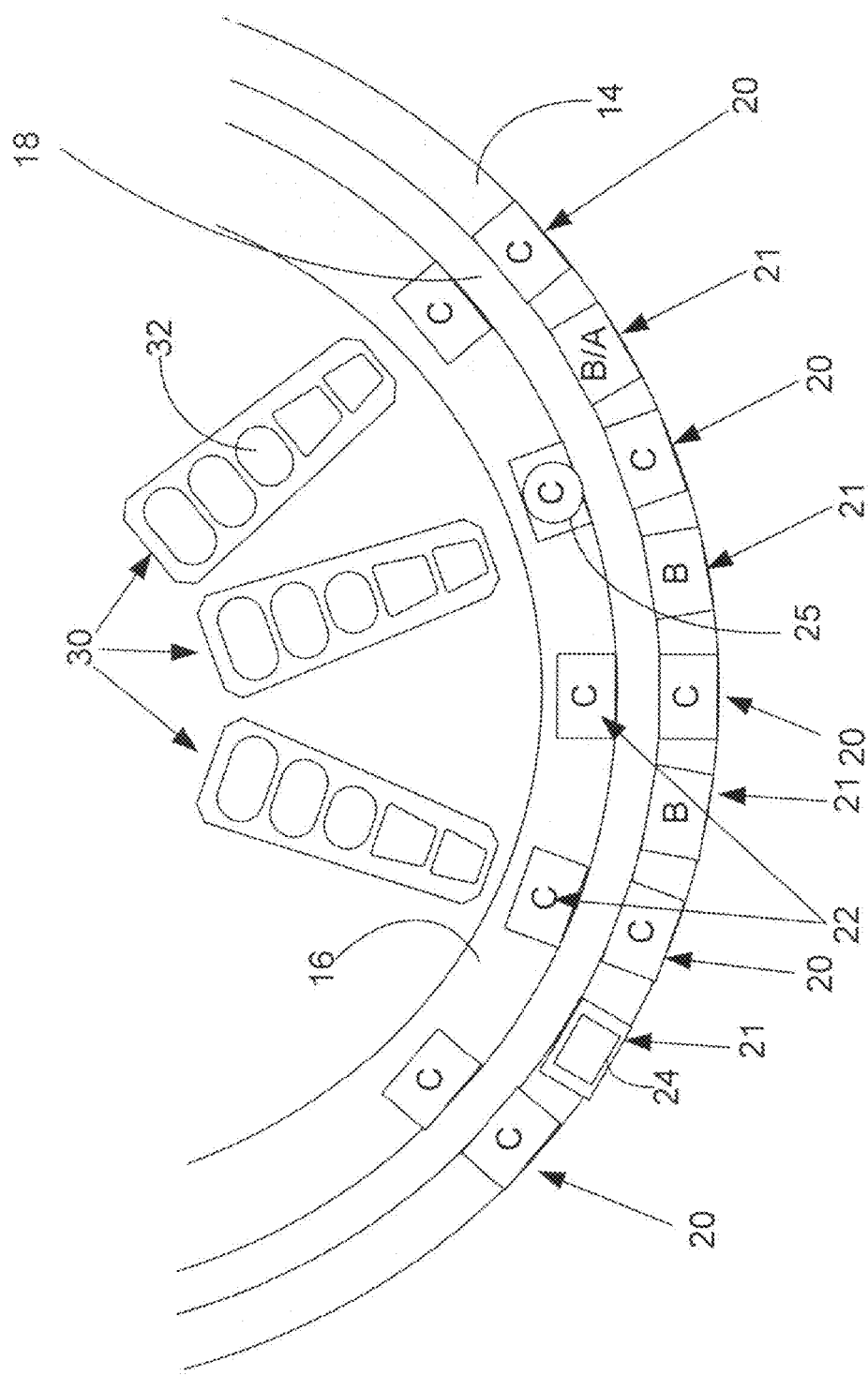
FIG. 2 is a simplified plan view of a portion of the analyzer of FIG. 1.

FIG. 1, taken with a simplified FIG. 2, shows schematically the elements of an automatic chemical analyzer 10 in which the present invention may be advantageously practiced, analyzer 10 comprising a reaction carousel 12 supporting an outer cuvette carousel 14 having cuvette ports 20 formed therein and an inner cuvette carousel 16 having vessel ports 22 formed therein, the outer cuvette carousel 14 and inner cuvette carousel 16 being separated by a open groove 18. Cuvette ports 20 are adapted to receive a plurality of reaction cuvettes 24 that contain various reagents and sample liquids for conventional clinical and immunoassay assays while vessel ports 22 are adapted to receive a plurality of reaction vessels 25 that contain specialized reagents for ultra-high sensitivity luminescent immunoassays. Reaction carousel 12 is rotatable using stepwise movements in a constant direction, the stepwise movements being separated by a constant dwell time during which carousel 12 is maintained stationary and computer controlled assay operational devices 13, such as sensors, reagent add stations, mixing stations and the like, operate as needed to perform the myriad of operations required to perform clinical assays on an assay mixture contained within a cuvette 24. Such devices and their operational control by a conventional microprocessor based computer 15 are well known in the art and need not be described herein.

An indexing drive for the reaction carousel 12 moves the reaction cuvettes in the constant direction a predetermined numbers of incremental steps. The length of the circumference of cuvette carousels 14 and 16, the separation distance between cuvette ports 20 and 21 and also between ports 22, the number of cuvette ports 20, 21 and 22, and the number of increments per indexing are selected so that any given cuvette port 20, 21 or 22 returns to its original starting position after a fixed number of incremental steps. Thus, all cuvette ports 20, 21 and 22 on the reaction carousel 12 return to their original location in a full operational cycle time, hereinafter identified as "CT", which is determined by the fixed number of incremental steps multiplied by the sum of dwell time at each assay device and the time required for a stepwise movement. This predetermined movement cycle facilitates the precise tracking by computer 15 of each and every cuvette port 20, 21 and 22 and reaction cuvettes 24 contained therein, including having historical data concerning the types of assays conducted in each and every reaction cuvette 24.

FIG. 2 further illustrates a layout of carousel 12 in which ports 22, marked "C" are dedicated exclusively to the use of Type C assays, described hereinafter, and are equally spaced along the circumference of cuvette circle 16 in radial alignment with alternate cuvette ports 20 equally spaced along the circumference of cuvette circle 14. In contrast, cuvette ports 20 and 21 are useful for Type C assays as well as Type B and Type A assays, also described hereinafter. In an advantageous embodiment, every other cuvette port 20 is dedicated exclusively to the use of Type C assays, also marked "C", and the intervening alternate cuvette ports 21 are dedicated to the use of Type B, marked "B", and Type A assays. For the purpose of illustration, a single cuvette port 21 is marked "B/A" to indicate that a certain port 21 may be initially used to therein perform a certain Type B assay and after that certain Type B assay is completed, that certain port 21 may be subsequently used to therein perform a certain Type A assay during a single full operational cycle time CT.

Analyzer 10 is controlled by software executed by the computer 15 based on computer programs written in a machine language like that used on the Dimension® clinical chemistry analyzer sold by Dade Behring Inc, of Deerfield, Ill., and widely used by those skilled in the art of computer-based electromechanical control programming. Computer 15 also executes application software programs for performing assays conducted by various analyzing stations 17 within analyzer 10. Analyzing stations 17 may be located proximate outer reaction carousel 12 and are adapted to measure light absorbence in or emission from cuvettes 24 at various wavelengths, from which the presence of analyte in the sample liquid may be determined using well-known analytical techniques. Stations 17 typically comprise conventional photometric, fluorometric or luminescent measuring devices adapted to perform an interrogating measurement at any convenient time interval during which reaction carousel 12 is stationary.

Figure 5A:
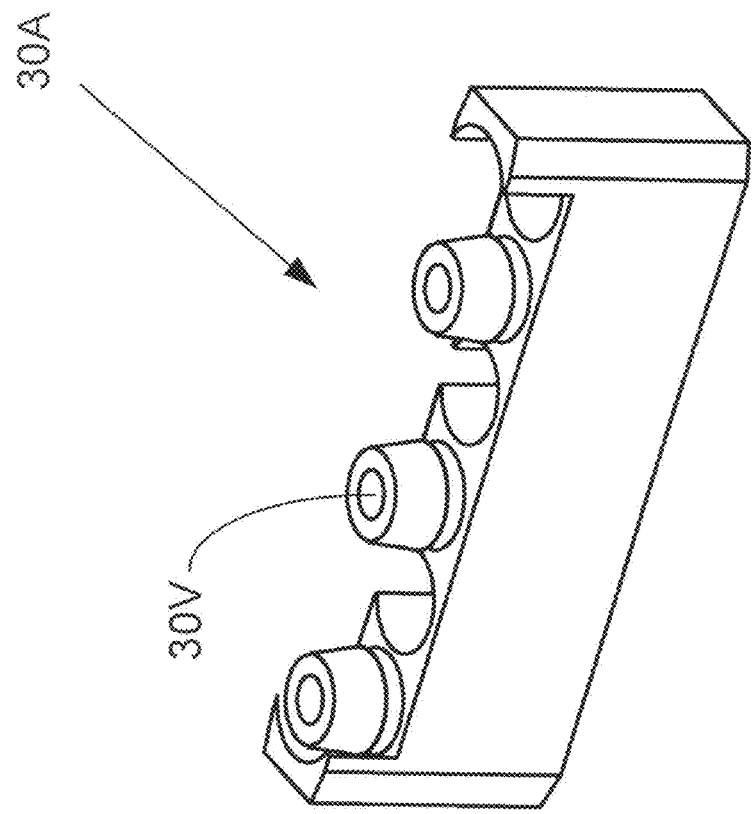
FIG. 5A is a perspective view of a vial carrier useful in the analyzer of FIG. 1.
Figure 5:
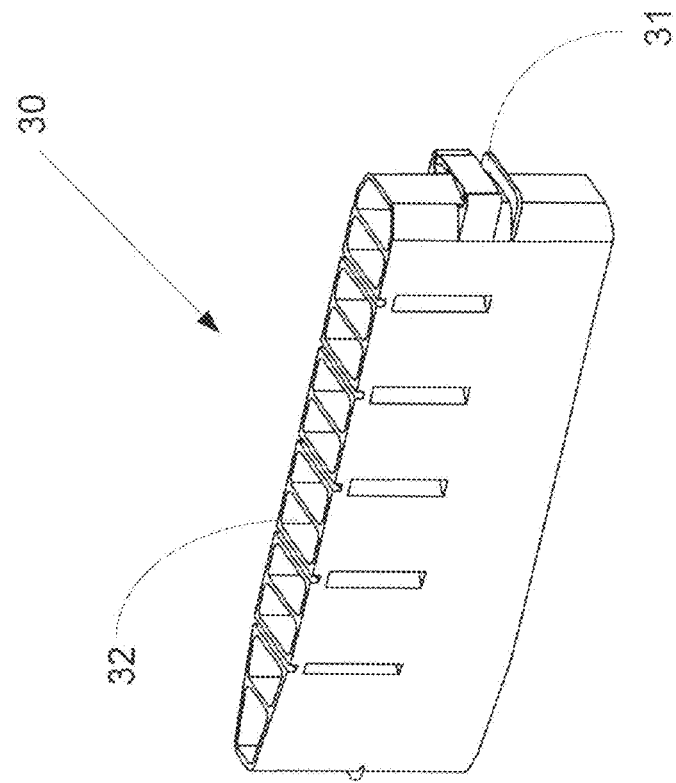
FIG. 5 is a perspective view of a reaction container useful in the analyzer of FIG. 1.

Temperature-controlled reagent storage areas 26, 27 and 28 store a plurality of multi-compartment elongate reagent cartridges 30 like that illustrated in FIG. 5 and described in co-pending application Ser. No. 09/949,132 assigned to the assignee of the present invention, or vial carriers 30A seen in FIG. 5A, and containing reagents in wells 32 as necessary to perform a given assay. A lock-out device 31 is provided to prevent accidental re-use of a previously used reagent container 30. As described later, reagent storage area 26 comprises a first reagent operation carousel 26A, from which reagent cartridges 30 may be moved for reagent preparation operations like hydration and remix, and a second reagent operation carousel 26B, in which reagent cartridges 30 are inventoried for access by a reagent aspiration and dispense arms 60. FIG. 1 shows an embodiment in which first reagent operation carousel 26A and second reagent operation carousel 26B are circular and concentric, the first reagent operation carousel 26A being inwards of the second reagent operation carousel 26B. Reagent containers 30 or reagent vial carrier 30A may be loaded by an operator by placing such containers 30 or carriers 30A into a loading tray 29 adapted to automatically translate containers 30 or carriers 30A to a shuttling position described later. Reagent vial carriers 30A contain solutions of known analyte concentrations in vials 30V and are used in calibration and quality control procedures by analyzer 10.

A bi-directional incoming and outgoing sample tube transport system 36 having input lane 34A and output lane 34B transports incoming individual sample tubes 40 containing liquid specimens to be tested and mounted in sample tube racks 42 into the sampling arc of a liquid sampling arm 44. Liquid specimens contained in sample tubes 40 are identified by reading bar coded indicia placed thereon using a conventional bar code reader to determine, among other items, a patient's identity, the tests to be performed, if a sample aliquot is to be retained within analyzer 10 and if so, for what period of time. It is also common practice to place bar coded indicia on sample tube racks 42 and employ a large number of bar code readers installed throughout analyzer 10 to ascertain, control and track the location of sample tubes 40 and sample tube racks 42. Such reader devices and the techniques for tracking are well known in the art and are not shown in FIG. 1 nor discussed further.

Figure 3:
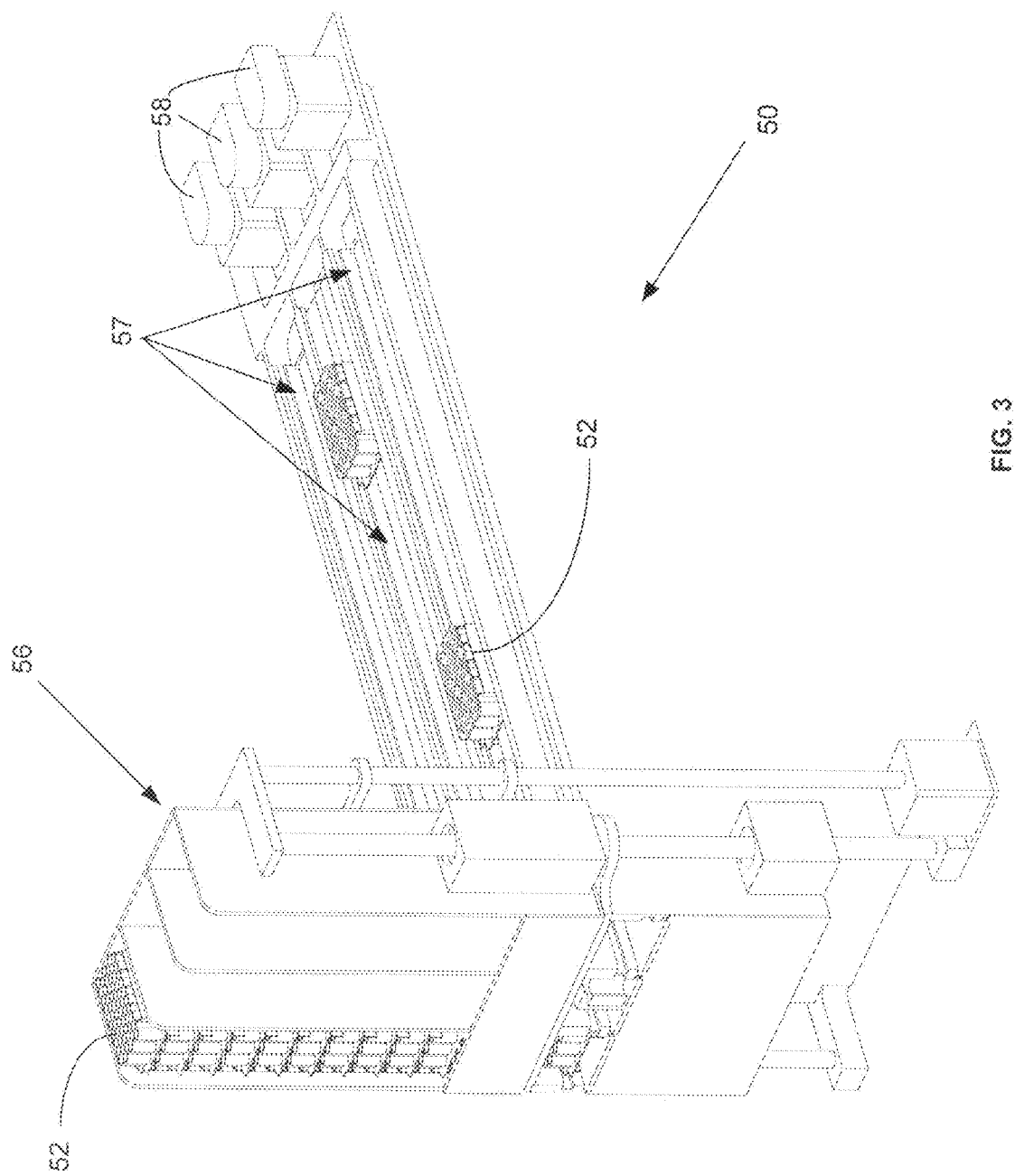
FIG. 3 is a perspective elevation view of an automated aliquot vessel array storage and handling unit of the analyzer of FIG. 1.
Figure 4:
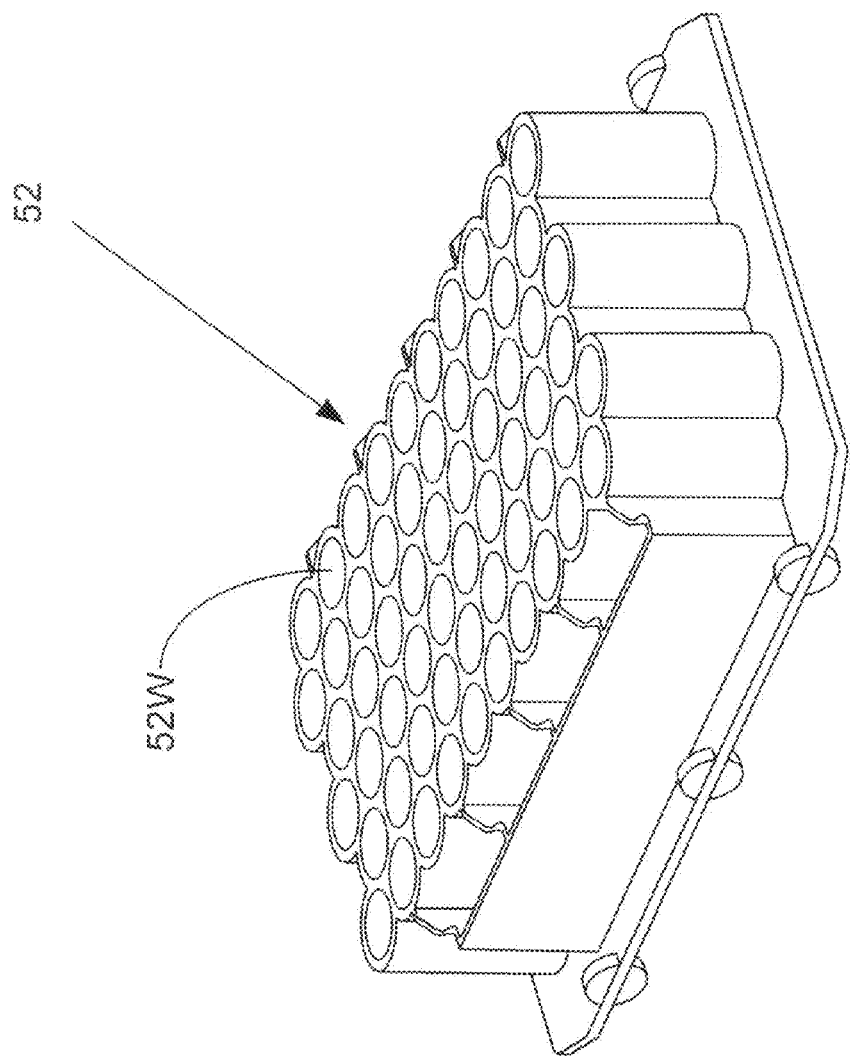
FIG. 4 is perspective elevation view of an aliquot vessel array useful in the analyzer of FIG. 1.

Sampling arm 44 supports a liquid sampling probe 46 mounted to a rotatable shaft 48 so that movement of sampling arm 44 describes an arc intersecting the sample tube transport system 36 and an aliquot vessel array transport system 50, as seen in FIG. 3. Sampling arm 44 is operable to aspirate liquid sample from sample tubes 40 and to dispense an aliquot sample into one or more of a plurality of vessels or wells 52W in aliquot vessel array 52, as seen in FIG. 4, depending on the quantity of sample required to perform the requisite assays and to provide for a sample aliquot to be retained by analyzer 10 within environmental chamber 38.

Aliquot vessel array transport system 50 comprises an aliquot vessel array storage and dispense module 56 and a number of linear drive motors 58 adapted to bi-directionally translate aliquot vessel arrays 52 within a number of aliquot vessel array tracks 57 below a sample aspiration and dispense arm 54 located proximate reaction carousel 12. Sample aspiration and dispense arm 54 is controlled by computer 15 and is adapted to aspirate a controlled amount of sample from individual vessels or wells 52W positioned at a sampling location within a track 57 using a conventional liquid probe 54P and then liquid probe 54P is shuttled to a dispensing location where an appropriate amount of aspirated sample is dispensed into one or more cuvettes 24 in cuvette ports 20 for testing by analyzer 10 for one or more analytes. After sample has been dispensed into reaction cuvettes 24, conventional transfer means move aliquot vessel arrays 52 as required between aliquot vessel array transport system 50, environmental chamber 38 and a disposal area, not shown.

A number of reagent aspiration and dispense arms 60, 61 and 62 comprising conventional liquid reagent probes, 60P, 61P and 62P, respectively, are independently mounted and translatable between reagent storage areas 26, 27 and 28, respectively and outer cuvette carousel 14. Probes 60P and 62P comprise conventional mechanisms for aspirating reagents required to conduct specified assays at a reagenting location from wells 32 in an appropriate reagent cartridge 30, the probes 60P, 61P and 62P subsequently being shuttled to a reagent dispensing location where reagent(s) are dispensed into reaction cuvettes 24 contained in cuvette ports 20 in outer cuvette carousel 14. Additional probes may be provided to provide increased flexibility if desired. A number of reagent cartridges 30 are inventoried in controlled environmental conditions inside reagent storage areas 26, 27 and 28; a key factor in maintaining high assay throughput of analyzer 10 is the capability to inventory a large variety of reagent cartridges 30 inside reagent storage areas 26A and 26B, 27 and 28 and to then quickly transfer random ones of these reagent cartridges 30 to reagenting locations for access by probes 60P, 61P and 62P.

Reaction cuvette load station 63 and reaction vessel load station 65 are respectively positioned proximate outer cuvette carousel 14 and inner vessel carousel 16 and are adapted to load reaction cuvettes 24 into cuvette ports 20 sideways as described later and reaction vessels 25 into vessel ports 22 using for example a translatable robotic arm 67. In operation, used cuvettes 24 in which an assay has been finally conducted, are washed and dried in a wash station 71 like disclosed in co-pending application Ser. No. 10/623,360 assigned to the assignee of the present invention. Subsequent assays are conducted in cleaned used cuvettes 24 unless dictated otherwise for reasons like disclosed in co-pending application Ser. No. 10/318,804 assigned to the assignee of the present invention. Cuvette unload station 59 is adapted to remove unusable reaction cuvettes 24 from cuvette ports 20 again using a translatable robotic arm 67 like seen on load stations 63 and 65.

Figure 6:
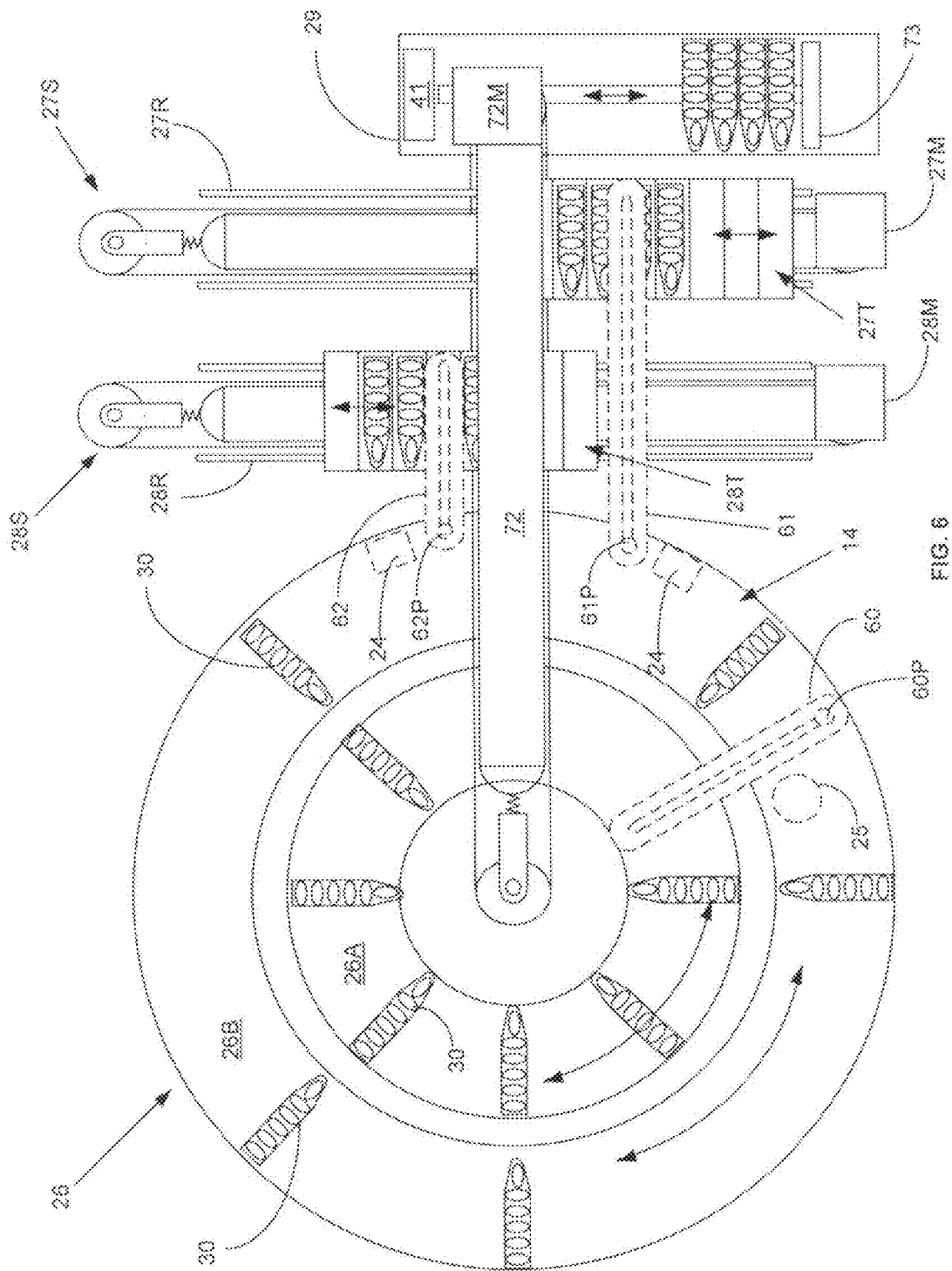
FIG. 6 is a top plan view of a random-access reagent container management system useful in the analyzer of FIG. 1.

FIG. 6 illustrates a single, bi-directional linear reagent container shuttle 72 adapted to remove reagent containers 30 from reagent container loading tray 29 having a motorized rake 73 that automatically locates containers 30 at a loading position beneath reagent container shuttle 72. Reagent containers 30 are identified by the type of assay chemicals contained in wells 32 using conventional barcode-like indicia and a bar-code-reader 41 proximate reagent container loading tray 29. Computer 15 is programmed to track the location of each and every reagent container 30 as it is transported within analyzer 10. Shuttle 72 is further adapted to dispose a reagent container 30 into slots in at least one slotted reagent container tray 27T or 28T within at least one reagent storage area 27 or 28, respectively. In a similar fashion, shuttle 72 is further adapted to remove reagent containers 30 from reagent container trays 27T and 28T and to dispose such reagent containers 30 into either of two concentric reagent carousels 26A and 26B within reagent storage area 26. Shuttle 72 is also adapted to move reagent containers 30 between the two concentric reagent carousels 26A and 26B. As indicated by the double-headed arc-shaped arrows, reagent carousel 26A may be rotated in both directions so as to place any particular one of the reagent containers 30 disposed thereon beneath reagent aspiration arm 60. Although reagent carousel 26B may also contain reagent containers 30 accessible by reagent aspiration arm 60, carousel 26B may be designated only for storing excess inventory of reagent containers 30 and vial containers 30A having calibration or quality control solutions therein. Any one of the reagent containers 30 disposed in reagent container trays 27T and 28T may be located at a loading position beneath reagent container shuttle 72 or at a reagent aspiration location beneath aspiration and dispensing arms 61 and 62, respectively, by reagent container shuttles 27S and 28S within reagent storage areas 27 and 28, respectively. Hereinafter, the term "server" is meant to define the combination of either reagent container shuttle 27S or 28S and either reagent storage area 27 or 28 and either reagent container tray 27T or 28T, respectively. Reagent container shuttles 27S and 28S are similar in design to reagent container shuttle 72. Reagent aspiration arms 60, 61 and 62 are shown in dashed lines to indicate that they are positioned above the surfaces of reagent containers 30 inventoried in carousel 26B, and reagent container trays 27T and 28T, respectively. Reaction cuvettes 24 supported in outer cuvette carousel 14 are also both shown in dashed lines to indicate that they are positioned above the surfaces of reagent containers 30.

From the foregoing description, it is clear that shuttle 72 may move reagent containers 30 between reagent container loading tray 29, reagent container trays 27T and 28T, and reagent carousels 26A and 26B; further, shuttles 27S and 28S may move reagent containers 30 in reagent container trays 27T and 28T to appropriate aspiration locations (or to a loading location beneath shuttle 72) and reagent carousels 26A and 26B may place any reagent container 30 beneath reagent aspiration arm 60. Analyzer 10 is thus equipped with a random access reagent supply system with the flexibility to position a large number of different reagent containers 30 at different aspiration locations. Shuttles 72, 27S and 28S are equipped with automatic tension controls like disclosed in co-pending application Ser. No. 10/623,311 assigned to the assignee of the present invention so that the time required for reagent supply in analyzer 10 is not a throughput limitation.

In operation of analyzer 10, and in accord with the present invention, analyzer 10 is operated in a manner that achieves high throughput irregardless of the incoming demand for assays, or assay load mix, of different assays required to be conducted for different samples presented to analyzer 10. For the purpose of further explanation, consider an exemplary embodiment of the present invention in which reaction carousel 12 comprises 184 cuvette ports 24 located in cuvette ring 14 and moves or advances step-wise in a single rotational direction (clockwise or counter-clockwise) a total of 77 cuvette positions during each machine cycle. Each step-wise movement of 77 cuvette positions is followed by a corresponding stationary dwell time. The combination of a step-wise movement and subsequent stationary dwell time comprise a machine cycle of 3.6 seconds and are equal in time, so that reaction carousel 12 moves step-wise for a total of 1.8 seconds and is subsequently stationary for a period of 1.8 seconds. The prime-number relationships between the numbers of 184 cuvette ports 72 and the number of 77 cuvette positions moved in each machine cycle is well known in the art (U.S. Pat. No. 5,352,612) from which it may be determined that after a total of 184 machine cycles occur, each and every cuvette port 24 is returned to its each and every original starting position, thereby defining a full carousel cycle of 184 machine cycles of duration 3.6 seconds; the full operational cycle time of carousel 12 thus comprises 662.4 seconds or approximately 11 minutes. It should be emphasized that the values used in this exemplary example are not restrictive and that the principles of the present invention may be applied to any similarly operable analyzer 10. It is only required that each and every cuvette port 24 is returned to its each and every original starting position in a constant amount of time.

It is known that throughput of analyzer 10 may be increased by partitioning of the assays to be performed into groups defined by the length of time required to complete those assays, as disclosed in U.S. patent application Ser. No. 09/917,132. To achieve these ends, liquid aspiration and dispense arm 60 located proximate reagent storage areas 26 is controlled by CPU 15, according to pre-programmed software, firmware, or hardware commands or circuits to remove reagent from cartridges 30 stored within reagent storage area 26 and to dispense aspirated reagent into cuvettes 24 for a first grouping of assays called Type C assays, Type C assays comprising all assays having multiple reagent events or for which final incubation and test readings are completed in an amount of time greater than one-half the full operational cycle time of carousel 12. Assuming the exemplary operational cycle time of carousel 12 as described above, analyzer 10 is capable of performing about 350 Type C assays per hour.

Aspiration and dispense arm 61 is similarly operable to remove reagents from cartridges 30 stored within reagent storage area 27 and to dispense aspirated reagent into cuvettes 24 for a second smaller grouping of fewer assays called Type B assays, Type B assays comprising all assays having two reagent events and for which final incubation and test readings can be completed by the analyzer in an amount of time less than about one-half the full operational cycle time of carousel 12. Assuming the operational cycle time of carousel 12 as described above, analyzer 10 is capable of performing about 500 Type B assays per hour.

Aspiration and dispense arm 62 is similarly operable to remove reagents from cartridges 30 stored within reagent storage area 28 and to dispense aspirated reagent into cuvettes 24 for a third smaller grouping of fewer assays called Type A assays, Type A assays comprising all assays having a single reagent event and for which final incubation and test readings can be completed by the analyzer in an amount of time less than about one-third the full operational cycle time of carousel 12. Assuming the exemplary operational cycle time of carousel 12 as described above, analyzer 10 is capable of performing about 500 Type A assays per hour.

FIG. 7 illustrates the aforementioned partitioning of assays capable of being performed by analyzer 10 into three time-dependent assay-categories. As a matter of convention, time t=0.0 seconds is defined as the moment of sample dispensing into a test cuvette 19; for the sake of simplicity, all three types of assays are shown as having a single reagent addition R1 at a fixed time before sample addition. FIG. 7 shows how Type A assays comprise an assay format having a single reagent event and a final reading, indicated by Rf, completed within about 130-140 seconds after sample addition. Similarly, Type B assays comprise an assay format having two reagent events and a final reading completed within about 330-350 seconds after sample addition. Finally, Type C assays comprise an assay format having at least one reagent even and a final reading completed within between about 350 and 560 seconds after sample addition. At any time, indicated by Rd, during the assays, a reaction vessel reading or analysis may be made by any of the devices 70.

Table 1 contains a limited but illustrative listing of typical clinical and immunoassays for various Type A, B and C analytes along with timing details for various reagent additions and device operations.

TABLE 1

| Assay | TYPE | R1/T1 | S | R2/T2 | Rx/Tx | Rd1 | Rd2 | Rf-Final |
|---|---|---|---|---|---|---|---|---|
| Albumin | A | −21.6 | 0.0 | n/a | | | | 124.7 |
| Alkaline Phosphatase | B | −21.6 | 0.0 | 220 | | 284.5 | | 342.1 |
| Ammonia | C | −21.6 | 0.0 | | 205.6 | 241.3 | | 450.1 |
| Blood Urea Nitrogen | A | −21.6 | 0.0 | n/a | | | | 124.7 |
| Calcium | A | −21.6 | 0.0 | n/a | | −27.9 | | 67.1 |
| Cholesterol (HDL) | C | −21.6 | 0.0 | | 147.5 | 141.1 | | 442.9 |
| Cholesterol (Total) | A | −21.6 | 0.0 | n/a | | | | 378.1 |
| C-Reactive Protein | B | −21.6 | 0.0 | N/a | | −22.3 | 31.1 | 228.3 |
| Complement 3 | C | −21.6 | 0.0 | 220 | | 44.1 | 189.5 | 430.1 |
| Creatine Kinase | B | −21.6 | 0.0 | n/a | | 226.9 | | 284.5 |
| Creatinine | A | −21.6 | 0.0 | n/a | | 29.7 | | 59.9 |
| Digitoxin | C | −21.6 | 0.0 | | 248.0 | | 426.9 | 450.0 |
| Direct Bilirubin | B | −21.6 | 0.0 | 220 | | 182.3 | | 277.3 |
| Gamma Glutamyl Transferase | A | −21.6 | 0.0 | n/a | | | | 110.3 |
| Gentamicin | B | −21.6 | 0.0 | | 175.3 | 44.9 | 58.9 | 359.9 |
| Glucose | A | −21.6 | 0.0 | n/a | | −27.9 | 103.1 | 178.3 |

TABLE 1-continued

| Assay | TYPE | R1/T1 | S | R2/T2 | Rx/Tx | Rd1 | Rd2 | Rf-Final |
|---|---|---|---|---|---|---|---|---|
| Lactate Dehydrogenase | A | −21.6 | 0.0 | n/a | | | | 124.7 |
| Lactic Acid | C | −21.6 | 0.0 | | 68.8 | 36.9 | | 658.9 |
| Methadone | A | −21.6 | 0.0 | | 119 | 150.9 | | 179.7 |
| Phenobarbital | C | −21.6 | 0.0 | 220 | | 29.7 | 182.3 | 442.9 |
| Phenytoin | B | −21.6 | 0.0 | | 67.4 | 44.1 | | 255.7 |
| Phosphorous | B | −21.6 | 0.0 | 220 | | 182.3 | | 342.1 |
| Prealbumin | B | −21.6 | 0.0 | | | −17.3 | 29.9 | 297.9 |
| Prostatic Acid Phosphatase | C | −21.6 | 0.0 | | 463.6 | | | 514.9 |
| Pseudocholinesterase | B | −21.6 | 0.0 | 220 | | 255.7 | | 284.5 |
| Salicylate | A | −21.6 | 0.0 | | 54.4 | 36.9 | | 88.7 |
| Total Bilirubin | C | −21.6 | 0.0 | 220 | | 182.3 | 342.1 | 450.1 |
| Total CO2 | A | −21.6 | 0.0 | n/a | | −40.9 | 20 | 59.9 |
| Transferrin | C | −21.6 | 0.0 | 220 | | 44.1 | 189.5 | 430.1 |
| Triglyceride | B | −21.6 | 0.0 | 220 | | | 255.7 | 284.5 |
| Valproic Acid | C | −21.6 | 0.0 | n/a | | 74.9 | 212.9 | 422.8 |

An example of analyzer 10 operating in a manner to advantageously perform the three assay type A, B, and C follows. Prior to the loading of a cuvette 24 with sample contained within aliquot wells 52W and to be tested using a Type A assay, a first reagent R1 is aspirated by arm 62 from an appropriate compartment of a reagent cartridge 30 within reagent storage area 28 and is deposited into a cuvette 24A within a cuvette port 21 at a time T1. At time T0, samples for which Type A assays are to be conducted are aspirated by probe 54P and deposited within the cuvette 24A preloaded with reagent R1.

In a similar manner, prior to the loading of a cuvette 24B with sample contained within aliquot wells 52W and to be tested using a Type B assay, a first reagent R1 is aspirated by arm 61 from an appropriate compartment of a reagent cartridge 24 within reagent storage area 27 and is deposited into cuvette 24B within a cuvette port 21 at a time T1. At time T0, samples for which Type B assays are to be conducted are aspirated by probe 54P and deposited within cuvette 24B. As mentioned above, in the instance of Type B assays, a second reagent addition may be accomplished at a time T2 after T0, again using arm 61 to access a reagent cartridge 30 within reagent storage area 27.

Finally, prior to the loading of a cuvette 24C with sample contained within aliquot wells 52W and to be tested using a Type C assay, a first reagent R1 is aspirated by arm 60 from an appropriate compartment of a reagent cartridge 24 within reagent storage area 26 and is deposited into cuvette 24C within a cuvette port 20 or 22 at a time T1. At time T0, samples for which Type C assays are to be conducted are aspirated by probe 54P and deposited within cuvette 24B. As mentioned above, in the instance of Type C assays, a second reagent or third addition may be accomplished at a time T2 after T0 and a time Tx before or after T0, again using arm 60 to access a reagent cartridge 24 within reagent storage area 26.

After the cuvettes 24 are loaded with the just described reagents and samples, reaction carousel 12 continues its stepwise clockwise movement during which machine cycles, assay operational devices 34 operate upon the mixture within the cuvettes 24 in cuvette ports 20, 21 and 22 according to the appropriate assay protocols.

Because Type B assays have been partitioned in a manner such that all such assays are completed in less than one-half of the time required for reaction carousel 12 to complete a full operational cycle time, cuvettes 24B containing completed Type B assays may washed in the outer cuvette circle 14 of the reaction carousel 12 by wash station 71 and made available for a second Type B assay or for a Type A assay, depending on the mixture of assay types required to be performed by analyzer 10. Cuvette ports 21 are marked "B/A" or "B/B" to signify this scheme. Reaction carousel 12 continues its stepwise clockwise movement, during which machine cycles conventional assay operational devices 34 operate upon the mixture within the cuvettes 24A containing Type A assays and in cuvettes 24C containing Type C assays according to the appropriate assay protocols until the reaction carousel 12 completes a complete a full operational cycle time and both the Type A assays and Type C assays are completed.

In comparison with conventional analyzers in which completed Type B assays would remain on reaction carousel 12 for a full operational cycle time and hinder analyzer throughput, this alternate processing method in which one medium time length assay, described as a Type B assay, and one shorter time length assay, described as a Type A assay, are both completed during the same operational cycle time as required for one longer time length assay, described as a Type C assay, is completed, thereby enhancing throughput of analyzer 10.

Figure 8:
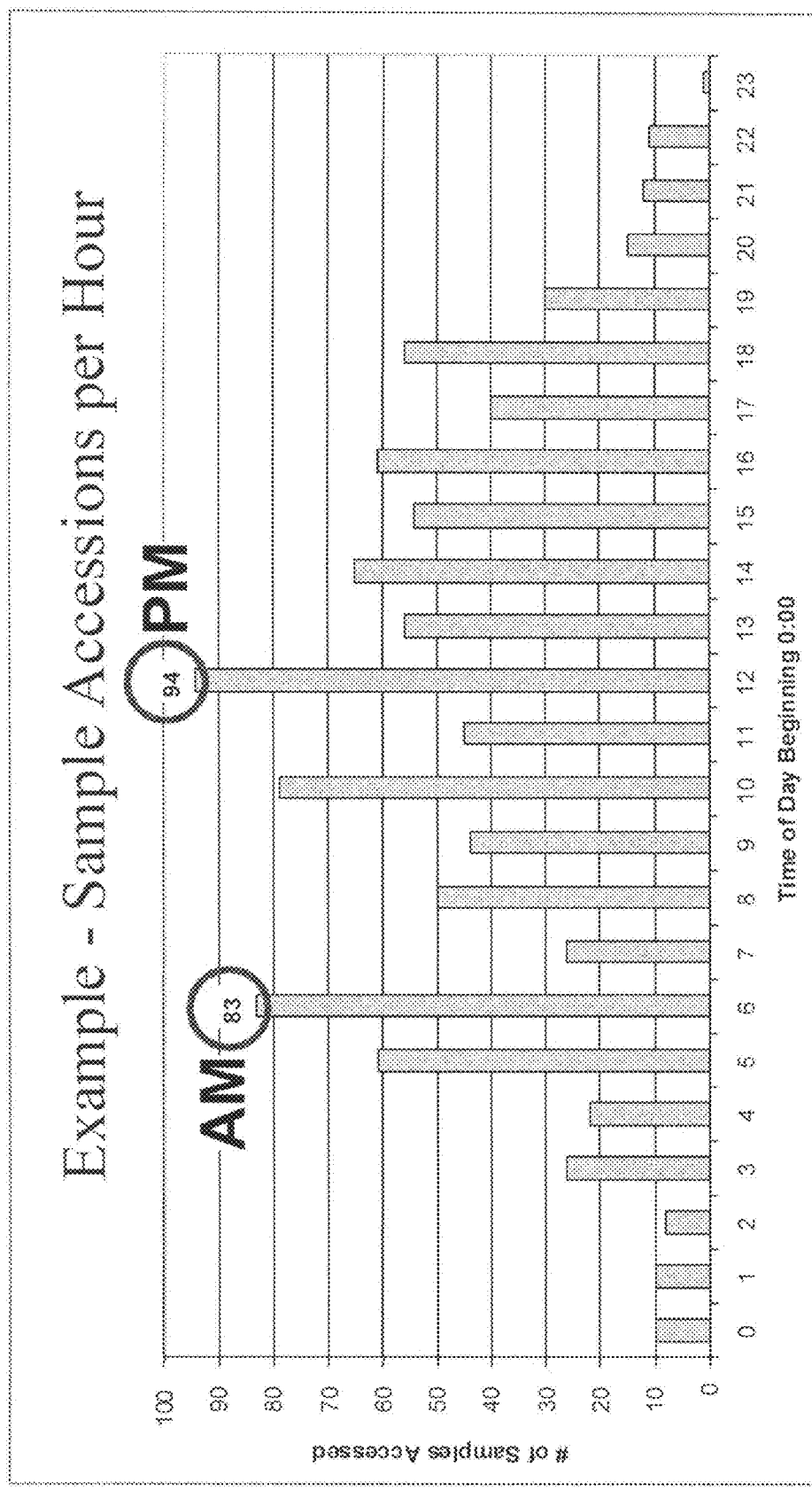
FIG. 8 illustrates a typical rate of incoming patient samples having assays to be conducted over a full 24-hour day within a clinic.

It has been found, however, that typical health care facilities experience a first demand pattern at the beginning of a day and a different second demand pattern towards the middle of a day. FIG. 8 illustrates the rate of incoming patient samples having assays to be conducted over a full 24-hour day. These are generally the two peak load periods within a day and while the numerical demand for assays is about the same, the pattern of assays requested is different. Actual experience at a "high volume" laboratory is illustrated in Table II below which shows that the percentage of Type C assays increases significantly but at the same time, the percentage of Type A assays decreases significantly. The "routine morning" mix of assays comprises 83 samples having a distribution of assays like shown in Table II.

TABLE 2

| | Type C | Type B | Type A |
|---|---|---|---|
| AM Morning Assay Demand Pattern | 17% | 15% | 68% |
| PM Afternoon Assay Demand Pattern | 35% | 19% | 46% |
| Relative Change | +106% | +27% | −32% |

It is clearly not advantageous with achieving high throughput irregardless of the mix of different assays required to be conducted to maintain a single assay operating protocol for analyzer 10. In particular, using a "morning-optimized" operating protocol defined above in the first example using the AM column of assay demand in Table 2, the throughput of analyzer 10 during the PM afternoon hours would then be reduced.

A key feature of the present invention is the discovery that if the reagent resources required to conduct a small number of selected high volume "routine morning" Type A assays are duplicated in more than one of the reagent servers 26, 27, or 28, then it is possible to optimize the throughput of "routine morning" assays at the beginning of a day as well as the throughput of "esoteric afternoon" assays hours later in that day. Thus, in addition to partitioning of assays into Type A, Type B or Type C assays so that multiple Type A and/or Type B assays may be fully performed during a single full operational cycle time, the present invention also adds reagents as necessary to perform selected Type A assays into the inventory of reagents into at least reagent server 26, previously reserved for Type C assays, and optionally also into reagent server 27, previously reserved for Type B assays.

Figure 9:
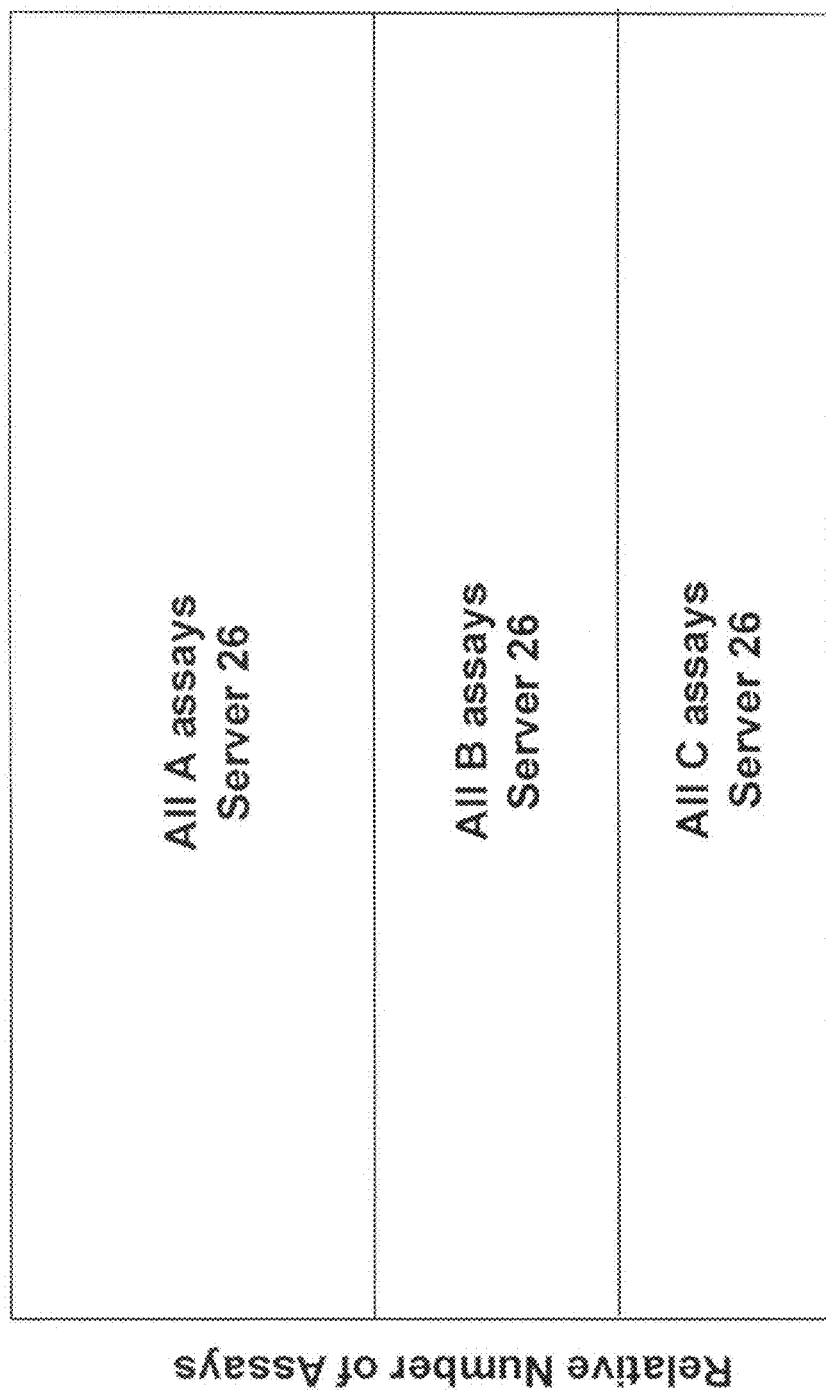
FIG. 9 illustrates a non-optimized partitioning of assays and reagents servers on the analyzer of FIG. 1; and, FIG. 9A illustrates an optimized partitioning of assays and reagents servers on the analyzer of FIG. 1 in accord with the present invention.

The present invention is practiced by initially identifying an "non-optimized" assay operating protocol like illustrated in FIG. 9 in which a subgroup of the high volume "routine morning" Type A assays is defined such that as many as possible of the reagents required for conducting such assays at the Afternoon Assay Demand Pattern are supplied from reagent server 28. In addition, a subgroup of Type B assays is defined such that as many as possible of the reagents required for conducting such assays at the Afternoon Assay Demand Pattern are supplied from reagent server 27. In this scheme, third reagent server 26 supplies reagents required for conducting a remaining third group of assays, wherein the first, second and third groups of assays comprise all assays analyzer 10 is equipped to conduct.

Figure 9A:
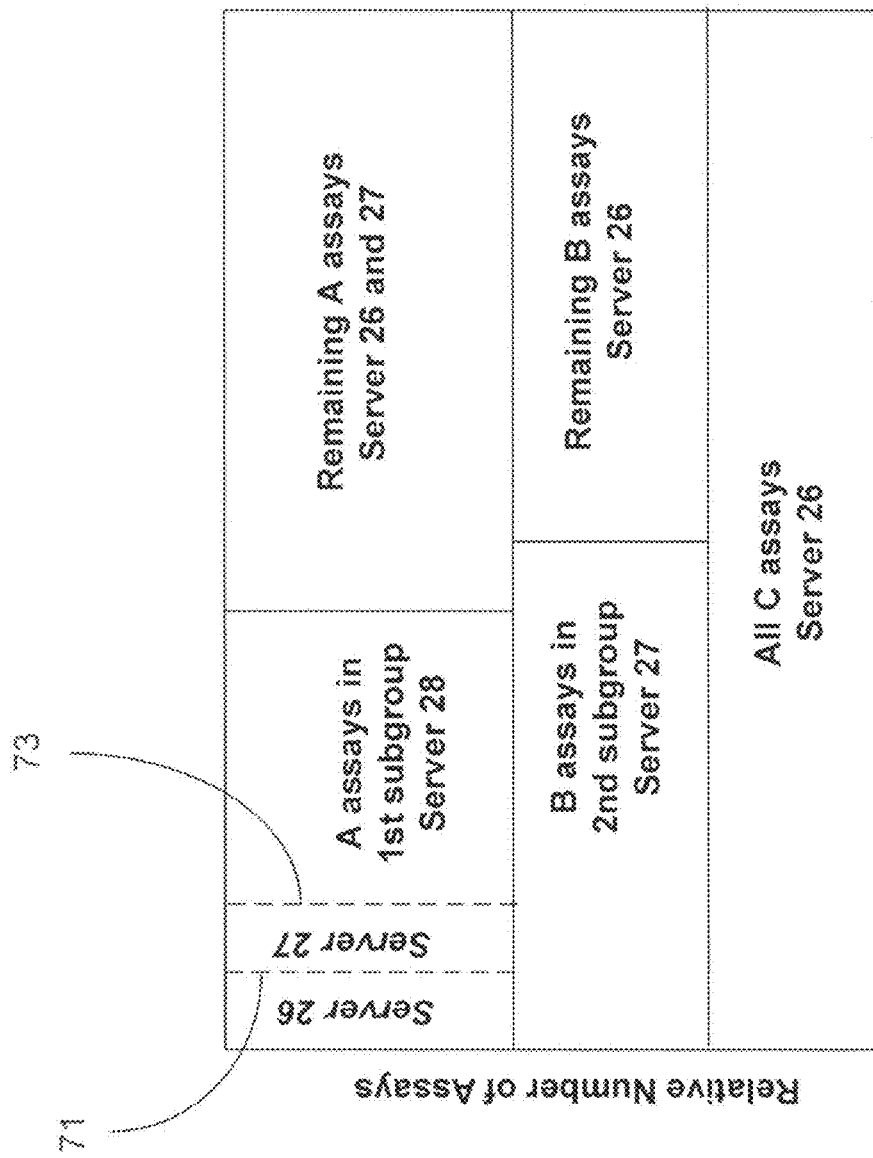

Subsequently, the throughput of analyzer 10 is optimized for both morning and afternoon assay demand patterns by duplicating within the inventory of reagents in reagent server 26 those additional reagents required for conducting the subgroup of high volume "routine morning" Type A assays at the Morning Assay Demand Pattern as illustrated in FIG. 9A. These certain assays (shared across servers) are selected from within the first subgroup of assays. This duplication of reagents is indicated in FIG. 8A by vertical dashed line 71 and the term "Server 26" in italics. Optionally, a selected portion of the reagents required for conducting the first subgroup of high volume "routine morning" Type A assays at the Morning Assay Demand Pattern may optionally also be duplicated within the inventory of reagents in reagent server 27 as indicated by vertical dashed line 73 and the term "Server 27" in italics. This novel reagent sharing protocol significantly enhances analyzer throughput since a sufficient quantity of the reagents required for conducting high volume "routine morning" Type A assays at the Morning Assay Demand Pattern is available on analyzer 10 so that no backlog of Type A assays exists during AM time period. It should be noted that server 26 is initially loaded or inventoried with a sufficient quantity of the reagents required for conducting Type C assays at the Afternoon Assay Demand Pattern and since the Morning Assay Demand Pattern for Type C assays is lower for such assays, server 26 has sufficient capacity to inventory both the additional reagents required for conducting the first subgroup of high volume "routine morning" Type A assays at the Morning Assay Demand Pattern as well as the reagents required for conducting Type C assays at the Afternoon Assay Demand Pattern. Consequently, analyzer 10 may be automatically operated by CPU 15 such that newly incoming Type A assays within the sub-group of high volume "routine morning" Type A assays are conducted using reagents from whichever reagent server 26, 27 or 28 has the smaller backlog of previously assigned assays from within said of high volume "routine morning" Type A assays.

As an illustration of the advantages of such an assay operating protocol, consider a typical health care facility having a morning hourly demand rate for "routine morning" assays depicted as AM and having a "esoteric afternoon" hourly demand rate for assays depicted as PM in Table 3, and having the associated assay format types in analyzer 10. In this first example, corresponding to FIG. 8, in which the throughput of analyzer 10 will be optimized for the AM column representative of the hourly demand for "routine morning" assays, the additive hourly demand for a first group of Type A assays comprises Total $CO_2$ (185/hr) and Glucose (170) and Creatinin (120) and Blood Urea Nitrogen (106) and Calcium (105) totals 686 Type A assays per hour which exceeds the 500 assay/hour capacity of analyzer 10 for Type A assays for the particular embodiment of analyzer 10 described above with reagents for Type A assays supplied from server 28. Consequently, during the morning time frame, analyzer 10 will have a backlog of 168 Type A assays per hour for these high demand assays.

In this non-optimum scenario, and during the same during the morning time frame, the additive hourly demand for Type B assays comprises Alkaline Phosphatase (55) and Triglyceride (45) and Phosphorous (28) and Direct Bilirubin (30) and C-Reactive Protein (8) and Creatine Kinase (5) and Gentamicin (5) and Phenyloin (3) and Pseudocholinesterase (O) which totals 151 Type B assays well within the capacity of analyzer 10 for the particular embodiment described above as about 500 Type B assays per hour.

Also, in this non-optimum scenario, and during the same during the morning time frame, the additive hourly demand for Type C assays comprises Total Bilirubin (74) and HDL Cholesterol (33) and Digitoxin (9) and Lactic Acid (3) and Prostatic Acid Phosphatase (3) and Ammonia (3) and Valproic Acid (3) and Transferrin (2) and Complement 3 (2) which totals 132 Type C assays per hour. Since server 26 (1) is initially inventoried with the reagents required for conducting Type C assays at the Afternoon Assay Demand Pattern which has an additive hourly demand for Type C assays comprising Total Bilirubin (152) and HDL Cholesterol (66) and Digitoxin (18) and Lactic Acid (6) and Prostatic Acid Phosphatase (6) and Ammonia (6) and Valproic Acid (6) and Transferrin (4) and Complement 3 (4) which totals 286 Type C assays per hour, then server 26 (1) is not fully utilized during the morning time frame as the analyzer 10 is capable of performing about 350 Type C assays per hour while the additive hourly demand for Type A and Type C assays totals 632 assays per hour while the capacity for performing Type A and Type C assays totals 850 assays per hour.

TABLE 3

| Assay | Type | AM Hourly Demand | PM Hourly Demand |
| --- | --- | --- | --- |
| Albumin | A | 41 | 28 |
| Alkaline Phosphatase | B | 55 | 70 |
| Ammonia | C | 3 | 6 |
| Blood Urea Nitrogen | A | 106 | 72 |
| Calcium | A | 105 | 71 |
| HDL Cholesterol | C | 33 | 66 |
| (Total) Cholesterol | A | 38 | 26 |
| C-Reactive Protein | B | 8 | 10 |
| Complement 3 | C | 2 | 4 |
| Creatine Kinase | B | 5 | 6 |
| Creatinine | A | 120 | 105 |
| Digitoxin | C | 9 | 18 |
| Direct Bilirubin | B | 30 | 38 |

TABLE 3-continued

| Assay | Type | AM Hourly Demand | PM Hourly Demand |
|---|---|---|---|
| Gamma Glutamyl Transferase | A | 35 | 24 |
| Gentamicin | B | 5 | 6 |
| Glucose | A | 170 | 116 |
| Lactate Dehydrogenase | A | 22 | 15 |
| Lactic Acid | C | 3 | 6 |
| Methadone | A | 2 | 1 |
| Phenobarbital | C | 2 | 4 |
| Phenytoin | B | 3 | 4 |
| Phosphorous | B | 28 | 36 |
| Prealbumin | B | 3 | 4 |
| Prostatic Acid Phosphatase | C | 3 | 6 |
| Pseudocholinesterase | B | 0 | 15 |
| Total Bilirubin | C | 74 | 152 |
| Total $CO_2$ | A | 185 | 126 |
| Salicylate | A | 2 | 1 |
| Transferrin | C | 2 | 4 |
| Triglyceride | B | 45 | 57 |
| Valproic Acid | C | 3 | 6 |

In contrast with the above and as depicted in FIG. 8A and Table 4, and as provided for by the present invention, server 26 will also inventory the reagents required to perform 168 high demand Type A assays per hour. In terms of this example of a typical health care facility, the total hourly capacity for "routine morning" assays to be conducted by analyzer 10 is optimized as 500 assays per hour for Type A assays from server 28;
168 assays per hour for Type A assays from server 26;
151 assays per hour for the Type B assays from server 27; and,
286 assays per hour for Type C assays from server 26, so that the total capacity of analyzer 10 is 1105 "routine morning" assays/hour.

During the Afternoon Assay Demand Pattern times, the additive hourly demand for Type A assays decreases as seen in Table 2 and comprises Total $CO_2$ (126/hr) and Glucose (116) and Creatinin (105) and Blood Urea Nitrogen (72) and Calcium (71) totals 490 Type A assays per hour which is within the 500 assay/hour capacity of analyzer 10 for Type A assays for the particular embodiment of analyzer 10 described above with reagents for Type A assays supplied from server 28. Consequently, during the afternoon time frame, analyzer 10 will not have a backlog of Type A assays.

During the same afternoon time frame, the additive hourly demand for Type B assays comprises Alkaline Phosphatase (70) and Triglyceride (57) and Phosphorous (36) and Direct Bilirubin (38) and C-Reactive Protein (10) and Creatine Kinase (6) and Gentamicin (6) and Phenyloin (4) and Pseudocholinesterase (15) which totals 242 Type B assays well within the capacity of analyzer 10 for the particular embodiment described above as about 500 Type B assays per hour.

Similarly, during the same afternoon time frame and as explained previously, the additive hourly demand for Type C assays comprises Total Bilirubin (152) and HDL Cholesterol (66) and Digitoxin (18) and Lactic Acid (6) and Prostatic Acid Phosphatase (6) and Ammonia (6) and Valproic Acid (6) and Transferrin (4) and Complement 3 (4) which totals 268 Type C assays per hour. Since server 26 (1) is initially inventoried with the reagents required for conducting Type C assays at the Afternoon Assay Demand Pattern, then server 26 is capable of performing all required Type C assays.

In terms of this example of a typical health care facility in which the total hourly capacity of analyzer 10 is optimized as seen by identifying certain exemplary Type A assays in Table 4 for both morning and afternoon assay demand patterns by duplicating within the inventory of reagents in reagent server 26 those additional reagents required for conducting a subgroup of high volume "routine morning" Type A assays, then the throughput of "esoteric afternoon" assays becomes:

490 assays/hour for Type A assays;
242 assays/hour for Type B assays; and,
268 assays per hour for Type C assays, so that the capacity of analyzer 10 is 1000 assays per hour in the afternoon time frame compared to the 1105 assays/hour in the morning time frame. In other words, the throughput of analyzer 10 may be optimized for both morning and afternoon assay demand patterns by duplicating within the inventory of reagents in reagent server 26 those additional reagents required for conducting a subgroup of high volume "routine morning" Type A assays within the Morning Assay Demand Pattern.

TABLE 4

| Assay | Type | AM Hourly Demand | PM Hourly Demand | "Original" Server | "Optimized" Server(s) |
|---|---|---|---|---|---|
| Blood Urea Nitrogen | A | 106 | 72 | 28 (3) | 28 (3) |
| Calcium | A | 105 | 71 | 28 (3) | 28 (3) |
| Creatinine | A | 120 | 105 | 28 (3) | 28 (3) |
| Total $CO_2$ | A | 185 | 126 | 28 (3) | 26 (1) and 28 (3) |
| Glucose | A | 170 | 116 | 28 (3) | 26 (1) and 28 (3) |

Furthermore, a key feature of the present invention is the additional advantage that analyzer 10 may be operated by CPU 15 so that for every newly incoming selected Type A assay having the required reagents in both of reagent servers 26 and 28, new patient samples may be assayed using reagents from whichever of the two reagent servers 26 and 28 has the shortest demand backlog, thereby improving the individual assay throughput times required for these selected Type A assays to be completed.

The details of performing a myriad of assays like those in Tables 1 and 3 within a clinical analyzer is a task regularly encountered within the art and need not be described herein. It is sufficient that the teachings of the present invention, that overall analyzer throughput may be improved by enabling certain selected assays to be conducted using reagents from at least two servers. It is further obvious to one skilled in the art that the above described method for operating a clinical analyzer so as to simultaneously increase throughput regardless of whether the incoming assay demand pattern has a larger portion of a first group of assays or a larger portion of a second group of assays in addition to enabling certain selected assays to be conducted using reagents from whichever of at least two servers has the shorter backlog of demand is not dependent upon the specific operating parameters of analyzer 10 in the examples above. For example, analyzer 10 may have a different arrangement of cuvette ports 20 and 21 that return to their original location in a full operational cycle time, a different operating pattern for reaction carousel 12, different assay throughputs, sample and reagent aspiration and dispense arms and the like without affecting the operational method disclosed herein. For these reasons, the present invention is not limited to those embodiments precisely shown and described in the specification but only by the following claims.

I claim:

1. An analytical analyzer adapted for automatically conducting a number of clinical assays on patient samples in reaction cuvettes, said analyzer comprising:

a reaction carousel supporting a cuvette carousel having cuvette ports adapted to receive a plurality of reaction cuvettes suitable for conducting clinical assays therein, wherein each and every cuvette port is returned to an original starting position in said carousel in a full operational cycle time of the carousel;

first, second, and third reagent servers inventorying reagents required for performing said clinical assays; and analyzer control means configured for partitioning the different assays to be conducted by the analyzer into
  (i) a first sub-group of assays consisting only of those assays having the highest frequency of being conducted by the analyzer;
  (ii) a third sub-group of assays consisting only of those assays having the lowest frequency of being conducted by the analyzer, and
  (iii) a second sub-group of assays consisting only of those assays not contained in either the first or third sub-groups of assays, wherein the third reagent server contains reagents needed for conducting the first, second, and third sub-groups of assays, the second reagent server consists only of those reagents needed for conducting the first and second sub-groups of assays, and the first reagent server consists only of those reagents needed for conducting the first sub-group of assays.

2. The analyzer of claim 1 wherein said first group of assays comprise assays that are completed in less that one half of said operational cycle time.

3. The analyzer of claim 2 wherein said second group of assays comprise assays that require more than one half of said operational cycle time to be completed.

4. The analyzer of claim 3 wherein said analyzer control means selects reagents from whichever of the at least two servers has the shorter backlog of demand with which to perform assays in the first pattern of assays.

* * * * *